United States Patent [19]

Herweck et al.

[11] Patent Number: 4,652,263

[45] Date of Patent: Mar. 24, 1987

[54] ELASTICIZATION OF MICROPOROUS WOVEN TUBES

[75] Inventors: Steve A. Herweck; Theodore Karwoski, both of Nashua, N.H.

[73] Assignee: Atrium Medical Corporation, Hollis, N.H.

[21] Appl. No.: 747,035

[22] Filed: Jun. 20, 1985

[51] Int. Cl.⁴ .............................................. A61F 2/06
[52] U.S. Cl. .................................. 623/1; 128/339 R; 139/421
[58] Field of Search .......................... 623/1, 11, 12, 66; 128/334 R; 66/178 A, 194–197; 139/421–423

[56] References Cited

U.S. PATENT DOCUMENTS

| | | | |
|---|---|---|---|
| 2,836,181 | 5/1958 | Tapp | 128/334 |
| 2,978,787 | 4/1961 | Liebig | 28/73 |
| 3,029,819 | 4/1962 | Starks | 128/334 |
| 3,096,560 | 7/1963 | Liebig | 623/1 |
| 3,105,492 | 10/1963 | Jeckel | 128/334 |
| 3,142,067 | 7/1964 | Liebig | |
| 3,337,673 | 8/1967 | Jeckel | 264/324 |
| 3,688,317 | 9/1972 | Kurtz | 3/1 |
| 3,853,462 | 12/1974 | Smith | 8/130 |
| 3,878,565 | 4/1975 | Sauvage | 3/1 |
| 3,986,828 | 10/1976 | Hoffman et al. | 8/115.5 |
| 4,055,201 | 10/1977 | Fowler et al. | 623/1 |
| 4,086,665 | 5/1978 | Poirier | 3/1.4 |
| 4,108,161 | 8/1978 | Samuels et al. | 128/1 |
| 4,164,045 | 8/1979 | Bokros et al. | 3/1.4 |
| 4,191,218 | 3/1980 | Clark et al. | 129/383 |
| 4,192,020 | 3/1980 | Davis et al. | 3/1.5 |
| 4,208,745 | 6/1980 | Okita | 3/1.4 |
| 4,306,318 | 12/1981 | Mano et al. | 623/1 |
| 4,313,231 | 2/1982 | Koyamada | 3/1.4 |
| 4,340,091 | 7/1982 | Skelton et al. | 139/383 |

FOREIGN PATENT DOCUMENTS

| | | |
|---|---|---|
| 3116026 | 11/1982 | Fed. Rep. of Germany ......... 623/1 |
| 854284 | 10/1956 | United Kingdom . |
| 829943 | 1/1975 | United Kingdom . |
| 2077107A | 5/1980 | United Kingdom . |

Primary Examiner—Richard J. Apley
Assistant Examiner—Gregory Beaucage
Attorney, Agent, or Firm—Lahive & Cockfield

[57] ABSTRACT

Disclosed are the product and method for making a macroscopically smooth, microporous, flexible, elastic tubular prosthetic device from a substantially non-elastic woven fabric tube. The method involves axially compressing the substantially non-elastic tube on a tight fitting cylindrical mandrel so that the individual axially oriented threads of the fabric form loops projecting radially outwardly between circumferential threads. The threads are set to return to this loop configuration upon release of tension applied axially to the tube. The exterior of the tube presents an easily deformed, macroscopically smooth surface having a multiplicity of interstices among the threads and among the fibers of the threads into which cells can grow after implantation.

15 Claims, 7 Drawing Figures

ELASTICIZATION OF MICROPOROUS WOVEN TUBES

BACKGROUND OF THE INVENTION

This invention relates to prostheses for implantation in an animal body and to the manufacture thereof. More particularly, the invention relates to macroscopically smooth, microporous, elastomeric tubular prosthetic devices and their manufacture from substantially non-elastomeric woven fabric tubes.

Vascular prosthetic devices are well known in the art and have been widely used in biomedical applications. The devices are used in reconstructive surgery, for example, where damaged blood vessels need to be replaced. Such prosthetic devices ideally should have the characteristic properties of natural blood vessels. Natural vessels are capable of returning to their original shape after being stretched, compressed, or bent and generally are not subject to kinking or radial collapse.

Vascular implants must be composed of biologically inert, biocompatible material. Materials that have been used in the past for prosthetic devices include Dacron (Dupont trademark for polyethylene terephthalate), Orlon (Dupont trademark for polyacrylonitrile), and Teflon (Dupont trademark for tetrafluoroethylene), though other materials may be appropriate.

Various prosthetic devices and methods of manufacture are known. Several patents, for example U.S. Pat. Nos. 2,836,181, and 3,142,067, disclose fabric tubes which are corrugated, crimped or folded to impart elasticity. In U.S. Pat. No. 3,337,673, a uniformly corrugated prosthetic device is disclosed. The device is formed by wrapping a tube with a filament at spaced intervals and pushing the ends of the tube toward each other. U.S. Pat. No. 3,096,560 discloses a prosthetic device with a smooth interior, but with a finely folded exterior structure. The problem, however, with these devices is that rough or sharp crimps and corrugations may irritate tissue surrounding the implant and thus hinder integration of the foreign implant into the animal body. The surface of natural blood vessels is smooth, and therefore a smooth implant free of crimps, corrugations and folds would be more like the natural vessel.

Accordingly, it is an object of this invention to provide a prosthetic device with improved characteristics for use as blood vessel replacement parts. Another object is to provide a macroscopically smooth, microporous, elastic prosthesis for implantation in animal bodies which need not be crimped, corrugated, or folded and to provide a process for making the prosthesis. Other objects are to provide a prosthesis which promotes integration of surrounding natural connective or other tissue, to provide a macroscopically smooth, microporous, elastic prosthesis with threads defining microscopic loops situated between circumferential threads, and to provide such a prosthesis which may be coated with a non-thrombogenic material resulting in a high degree of patency. Still other objects are to provide a prosthesis composed of biologically compatible and biologically inert material having a smooth, non-thrombogenic lumen resistant to shrinkage or collapse. Another object of the invention is to provide a prosthetic graft device with axially oriented fibers forming microscopic loops to increase the surface area per unit length of the graft and to provide elastic behavior, which device is porous but practically impermeable to blood and water. Yet another object is to provide a blood vessel replacement part which facilitate anastomosis and handling by the surgeon.

These and other objects of the invention will be apparent from the drawing, claims, and description which follow.

SUMMARY OF THE INVENTION

There has now been discovered a macroscopically smooth, microporous, elastic tubular prosthetic device for implantation in an animal body produced from a substantially non-elastic tubular woven fabric. The device contains axially oriented warp threads forming loops extending radially outwardly between circumferential fill threads. The loops are set to return to the loop configuration upon release of tension applied axially to the tube.

The device is prepared from a microporous woven fabric tube composed of circumferentially oriented fill threads interwoven with substanially non-elastic axially oriented warp threads. The tube is moistened and placed on a smooth, hard-surfaced cylindrical mandrel with an outside diameter substantially equal to the inside diameter of the tube. The tube is placed coaxially over the cylindrical outer surface of the mandrel so that the inside surface of the tube is uniformly in contact therewith. Next, the tube is progressively compacted axially on the mandrel so that the axially oriented warp threads form loops extending radially outwardly from between circumferentially-oriented threads. The tube is then heated or otherwise treated on the mandrel to set the loop configuration, thus providing the threads with "memory" and allowing the axially oriented threads to return to the loop configuration upon release of tension applied axially to the tube.

Optionally, the tube may be provided with a helical winding, e.g., of a polypropylene monofilament about its outer surface. In preferred embodiments, the fabric of the tube is a polyethylene terephthalate polymer and the threads are coated with a thin film of a non-thrombogenic material such as a fluorine-containing polymer, most preferably a cross-linked coating of a fluorine-containing polymer covalently bonded to all surfaces of the threads applied by a plasma polymerization technique. Preferably, the product of the invention has a stretch length 20% to 70% greater than its unstretched length.

BRIEF DESCRIPTION OF DRAWING

Like reference characters in the respective drawn figures indicate corresponding parts. The dimensions of the threads and their spacing in FIGS. 1 and 2 of the drawing are not to scale but rather have been drawn to promote clarity of description.

DESCRIPTION OF THE INVENTION

Figure 1:
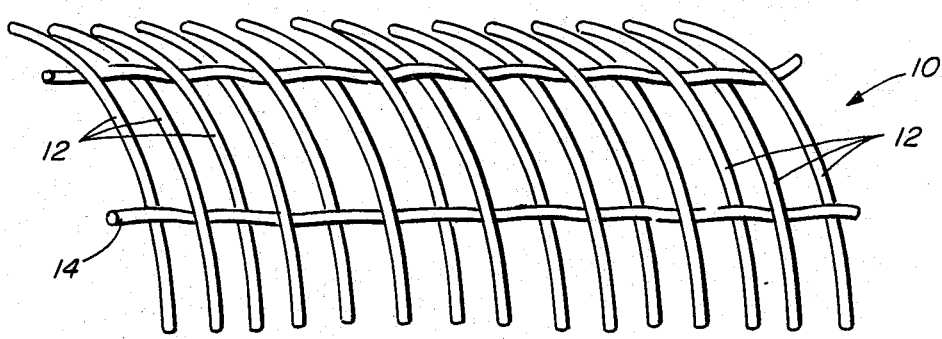
FIG. 1 illustrates schematically a portion of an interwoven fabric tube before treatment in accordance with the invention.
Figure 1A:
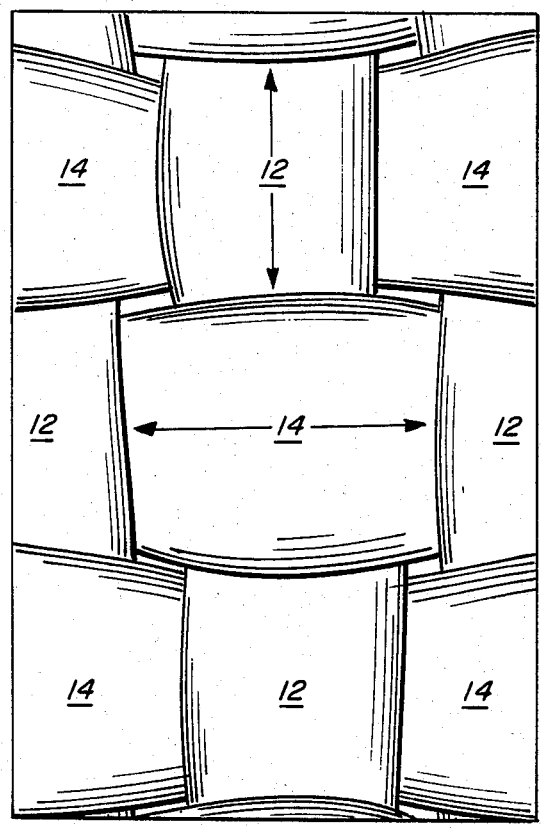
FIG. 1A shows a portion of an interwoven fabric tube before treatment in accordance with the invention as it appears under the microscope.

Referring to the drawing, FIGS. 1 and 1A illustrate a section of a fabric tube 10 before treatment in accordance with the invention. It comprises a multiplicity of circumferentially-oriented, fill threads 12 interwoven in a one over one relationship with longitudinally oriented non-elastic warp threads 14. The fill threads 12 and warp threads 14 may comprise any non-inflamatory synthetic fibrous material, twisted, texturized, or braided yarn or monofilament. Preferably, however, the threads comprise a material which is relatively non-inflamatory when implanted. Thus, various polyesters, polyamides, polyethylenes, fluorinated fibers and various other known polymeric threads may be used. The currently preferred material is polyethylene terephthalate, e.g., material sold by E. I. du Pont de Nemours Co. under the trademark Dacron.

In the practice of the invention, it is preferred to employ threads made of one or more yarns, each of which comprise intertwined and/or twisted fine fibers which have a diameter dimension less than about 15 microns, most preferably less than 7 microns. The small size of the fibers making up the yarns and threads is believed to be responsible in part for the outstanding patency of prosthetic devices made with tubes constructed in accordance with the invention.

The woven tube shown in FIGS. 1 and 1A is illustrative only, and other types of weaves can be treated with success in accordance with the invention. Thus, the one-over-one weave shown could be replaced, for example, with a two-over-one, one-over-two, or two-over-two weave. Other types of weaves may be used provided their threads have a circumferential component which defines the inside diameter of the tube and an axial component which can be formed into microscopic loops as disclosed hereinafter.

The currently preferred tube, shown in FIG. 1A, comprises fibers which are approximately 5-7 microns in the cross-section. The warp threads comprise 3 intertwined yarns each of which comprise 75 filaments or fibers to result in a yarn having a denier of 50. The fill threads are 96 filament single yarns having a denier of 100. The use of such materials in fabricating the tube to be treated results in a wall thickness approximately 0.3-0.6 mm as measured from the top of the loops to the inside surface of the tube after treatment. The fibers of the preferred embodiments of the invention are to be contrasted with currently available prosthetic tubes which are believed to comprise fibers of significantly larger cross-section.

The length and diameter of the original tube is selected according to biomedical need. Generally, the inside diameter of the tube may range from 3 mm to 2 cm. Smaller diameter tubes are possible.

Figure 2:
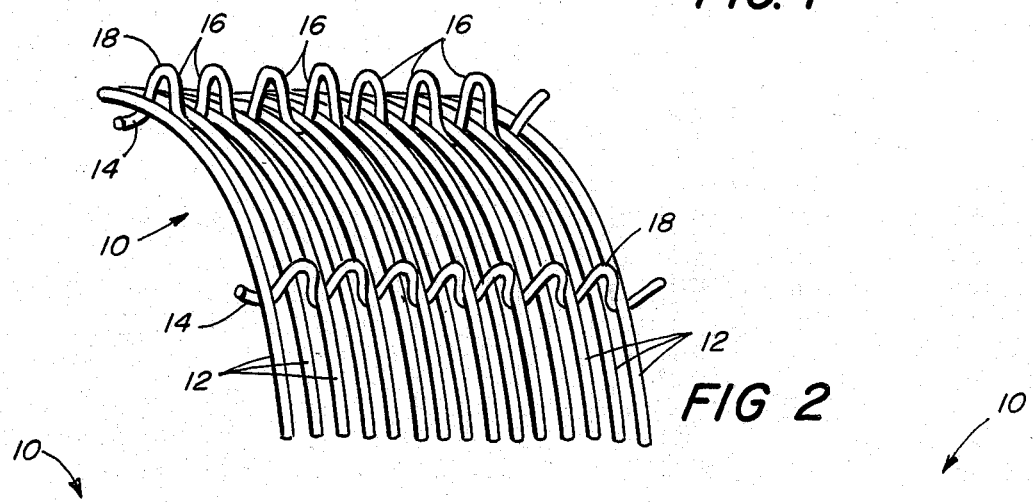
FIG. 2 illustrates schematically the fabric tube portion of FIG. 1 after treatment showing the axially oriented thread loops formed between the circumferential threads.
Figure 2A:
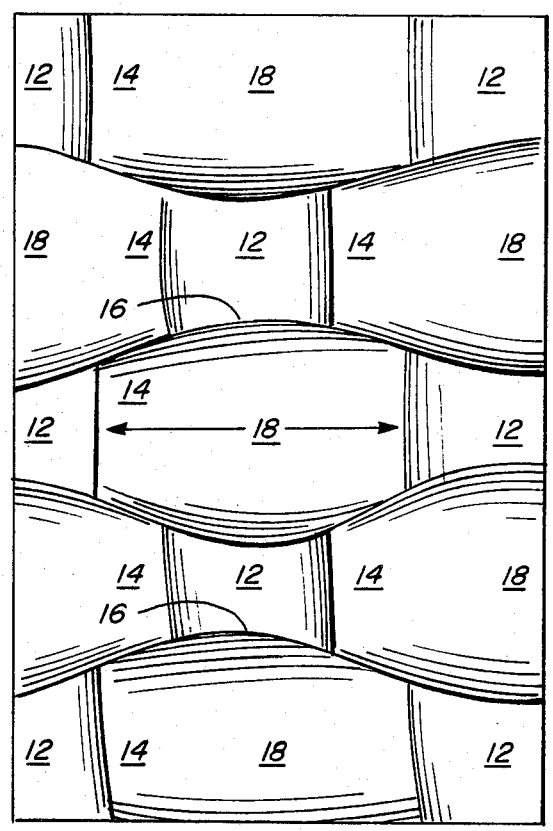
FIG. 2A shows the fabric tube portion of FIG. 1A after treatment in accordance with the invention as it appears under the microscope.

FIGS. 2 and 2A illustrate the same woven fabric tubular section depicted in FIGS. 1 and 1A after treatment in accordance with the invention. Note that the fill threads 12 have been moved closer together and axially compacted and that the warp threads 14 have been formed into loops 16 extending radially upwardly from between the fill threads such that each loop has a single fill thread therebeneath. The top portions 18 of the loops 16 together define a macroscopically smooth surface which visually appears and when touched feels very similar to the non-treated tube. However, tubes treated in accordance with the invention can typically be stretched 20%-70% of their non-stretched, compacted length.

To convert the fabric tube of FIGS. 1 and 1A into that shown in FIGS. 2 and 2A, the tube is moistened and placed on a smooth, cylindrical mandrel having an outside diameter substantially equal to the inside diameter of the tube. The mandrel preferably comprises Teflon (du Pont trademark for polytetrafluoroethylene resin), though mandrels composed of other materials may be used. The tube is smoothed out over the mandrel such that the entirety of its inside surface is in contact therewith and then treated, e.g., heated to a temperature of 380° F. for 15 minutes in a convection oven. This heating step is optional but has been found to preset the smooth inner surface. The tube is then allowed to cool back to room temperature and compacted on the mandrel by progressively axially compressing the tube. This is done manually or mechanically to obtain the effect of the invention.

It is important that the fit between the tube and the mandrel be such that compaction results only in radial extension of the warp fibers upwardly to form the desired loops. A mandrel of insufficient diameter may result in crimping or folding of the fabric, as opposed to the threads of the fabric. The formation of the loops in the threads is responsible for imparting to the tube both a macroscopically smooth exterior surface and the elastic properties characteristic of the prosthetic devices of the invention. Generally, the tube is compressed axially to about 60% of its original length, that is, compactly enough to form the loops but not so compact that wrinkles or folds in the fabric, as opposed to the threads, result. The amount of compaction will vary depending on the degree of elasticity desired in the product, on the diameter of the threads, and on the tightness of the weave.

The height and spacing of the loops depends on several factors which include the thickness of the material of the threads, the tightness of the weave, and the length to which the original tube is reduced by compaction.

The fibers are then set in the loop-oriented, compacted form by conventional treatment with a reagent, heat, or some combination thereof while on the mandrel. Using the preferred polyethylene terephthalate threads of the invention, excellent results have been achieved by heating the compacted tube to 380° F. for 5-10 minutes. Of course, the temperature to which the tube is heated or whether a reagent treatment is used depends on the particular material from which the threads are made.

The product is a macroscopically smooth, microporous elastic tube section. The loops formed between fill threads return to the loop configuration upon release of tension applied axially to the tube. The loops are smooth and porous because of the fine fibers preferably used, and the compacted fabric has multiple interstices of various dimensions uniformly about its surface which receive connective or other tissue ingrowth after implantation. These features facilitate the integration of the tube into surrounding natural tissue upon implantation. The interior surface of the tube is a smooth, porous wall defined by the close-spaced fill threads 12 and the compacted warp thread portions anchoring the loops 18, all of which have been set on the mandrel while in close contact therewith.

Figure 3:
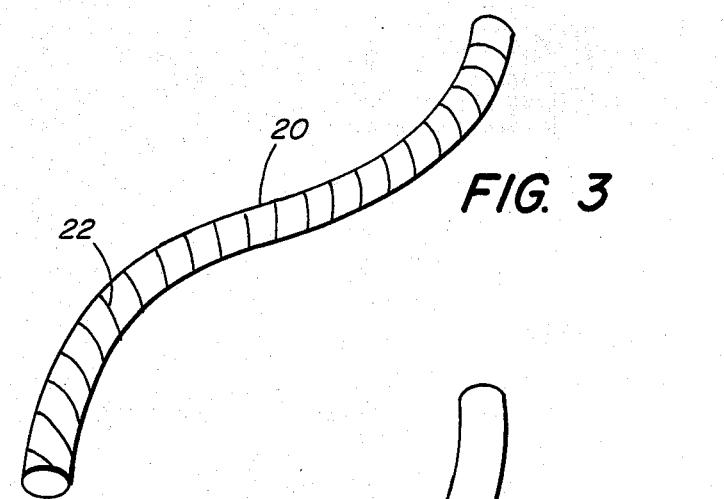
FIG. 3 illustrates a first embodiment of the invention.
Figure 4:
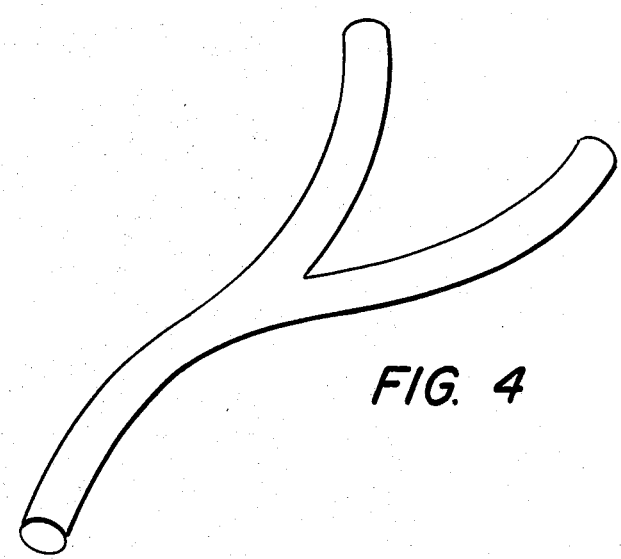
FIG. 4 illustrates a second embodiment of the invention.
Figure 5:
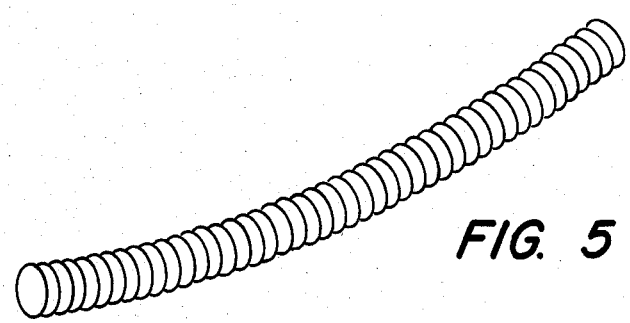
FIG. 5 illustrates a third embodiment of the invention.

FIGS. 3, 4, and 5 illustrate various prosthetic products which can be elasticized from woven fabrics of the type described above in accordance with the invention. FIG. 3 depicts a smooth, elastic tube 20 which forms kink-free bends. Tube 20 is helically wrapped with a polypropylene monofilament 22, an optional feature of prostheses made in accordance with the invention.

FIG. 4 represents a bifurcated tube which can be constructed in accordance with the foregoing teaching for use in replacement of branching veins or arteries. T shapes may also be fabricated. Bifurcated mandrels designed for the purpose having releasable cylindrical arms may be used to conduct the compaction technique.

FIG. 5 represents still another embodiment of the invention comprising a corrugated tube made from the macroscopically smooth tube produced as disclosed above. The prosthetic blood vessel of FIG. 5 may be fabricated, for example, by threading a previously formed, elasticized tube of the type disclosed herein over a mandrel having an outside diameter slightly smaller than the inside diameter of the tube, tying the tube with a helical or other filament wrap, and then compacting the fabric to produce the corrugated macroscopically compacted shape. The tube may then be heat set or otherwise treated to provide "memory" and will exhibit an elasticity even greater than the smooth surface tube of FIG. 3.

Elasticized tubes embodying the invention may be used as is for vascular replacement in animals and will show outstanding patency as compared with conventional tubes of the same material. However, it is preferred to coat all surfaces of each of the threads of the compacted, elasticized tube by a plasma-coating process which deposits a cross-linked coating of one or more fluorine-containing polymers bonded to all surfaces of the tube. The preferred method of coating generally involves continuous exposure of successive regions of the tube to a radio frequency field while maintaining a suitable subatmospheric pressure about the tube and exposing the tube surfaces to a source of a polymerizable fluorine containing gas such as tetrafluoroethylene gas. Further details of the preferred method of coating are disclosed in co-pending application Ser. Nos. 747,034 and 747,011, filed on even date herewith. Other potentially useful surface treatments are disclosed in the patent literature.

After sterilization, for example, by ethylene oxide, the prosthesis of the invention may be used for blood vessel replacement. The tubes of the invention may also be adapted to serve as catheters or shunts designed for use temporarily or permanently within the body.

Prostheses constructed in accordance with the invention, suitable coated with a nonthrombogenic material such as a fluorine-containing polymer, have been implanted with success in experimental animals. Patency of the product is improved significantly as compared with tubular substrates of the prior art. In addition, the prosthetic devices of the invention facilitate anastomotic procedures and are easily manipulated during surgery. The devices are tear resistant and flexible. They resist radial collapse and when coated as preferred appear to be totally non-thrombogenic.

The currently preferred embodiments of the invention have a fluorocarbon polymer coating on their interior surfaces having a high fluorine to carbon atomic ratio generally greater than 0.9, preferably greater than 1.2, and most preferably greater than 1.5, i.e., 1.5–1.9. At least at the higher ranges of these ratios, the tubes appear to be totally non-thrombogenic. The exterior surfaces of the tube preferably also have a fluorocarbon coating, preferably having a lower fluorine to carbon ratio such as 0.5. Such surfaces appear to minimize irritation and promote healthy ingrowth of connective or other tissue into the interstices among the thread loops and into the interstices among the fibers making up the threads.

The invention will be further understood from the following nonlimiting example.

7.4 mm Coated Graft

A polyethylene terephthalate flat ribbon woven fabric tube of warp yarns (3 ply 50 denier/72 filaments) and fill yarns (single ply, 100 denier/96 filaments) in a simple weave pattern was loaded onto a teflon-coated stainless steel mandrel. The tube, having an inside diameter of about 6.5–7.0 mm, was loaded onto a 6.7 millimeter (outside diameter) mandrel. The contact between the mandrel and tube material was such that all fibers are pulled and stretched to create a smooth, consistent pattern, elimating any loose spots or wrinkling. The loaded mandrel was then heat set at 380° F. for 15 minutes to reduce further any looseness of the fabric and to create a smooth internal surface. After cooling, a monofilament of medical grade polypropylene was helically wrapped around the fabric for external support. The polypropylene wrapped fabric was then subjected to heat (380° F. for 5 minutes) to melt and subsequently attach the polypropylene to the fiber structure of the fabric. After cooling, the fabric was mechanically axially compressed so as to minimize the gap between individual circumferential threads or yarns creating a tightly compacted smooth internal surface in contact with the mandrel. The external threads not constrained from radial movement by the fixed wall of the mandrel were thereby deformed to produce radially outwardly spaced loops. These loops create an elasticity in the axial direction improving handling characteristics of the synthetic graft. This external surface also promotes good tissue anchoring while the internal surface maintains a smooth flattened blood contact surface. The compacted tube was then subjected to an elevated temperature (e.g., 360° F. for 3 minutes) to heat set this microscopic loop structure imparting a "memory" to the individual threads.

This compaction procedure converted a 110 cm tube which is inelastic to a 80 cm elastic tube.

After all processing steps, the compacted fabric tube was washed in pyrogen-free detergent water to remove any contaminants. After drying and dehumidification, the elastic fabric tube was ready for coating.

The fabric tube was then loaded into a glass tube that forms the reaction vessel of the plasma deposition system. The ratio of the inside diameter of the glass tube to outside diameter of the fabric tube was about 1.1 to 1. In this case, the outside diameter of the compacted fabric tube was about 8.1–8.3 mm, and the inside diameter of the glass tube was about 8.9 mm. A vacuum of $3 \times 10^{-3}$ mm Hg was then imposed on the plasma system by pumping out gas from one end of the tubular reactor to substantially eliminate any oxygen present. A monomer gas, in this case tetrafluoroethylene, was fed into the system by a mass flow controller from the other end of the tube. The gas flow rate was 7 standard cubic centimeters per minute. The pumping speed and rate was adjusted to produce a system pressure of 500 millitorr at the inlet end and about 300 millitorr at the outlet end.

The pressure drop through the tube between the upstream and downstream ends creates a fluorine to carbon ratio gradient and an uneven thickness of polymer deposited onto the fabric tube due to varying energy and mass at each point. These variations over the length of the tube are no greater than about 10–12%. The F/C ratio of the coating ranged on the inside of the tube from 1.6–1.8. To control the F/C ratio further, the mass flow of monomer gas may be adjusted relative to the position of the energy input of the system so that the number of molecules polymerized is independent of the location or length of the plasma zone.

The energy input or discharge power is supplied by a pair of 6.3 mm wide aluminum band electrodes with an air gap of 2.5 cm which restricts the plasma zone. The electrodes were mounted on a traveling block which traverses the length of the tube to be coated at a speed of one cm per seven seconds. A power input of 50 watts was used. The coating is approximately 300 angstroms thick. A portion of the monomer gas passing through the tube traverses its pores. This results in a fluorinated coating on the outside surface of the tube which has a lower F/C ratio than the inside coating. After plasma polymerization, the elastic synthetic artery is removed from the reactor system, packaged, and sterilized.

The invention may be embodied in other specific forms without departing from the spirit and scope thereof. Accordingly, other embodiments are within the following claims.

What is claimed is:

1. An elastic prosthetic device for implantation in an animal body, said device comprising a microporous fabric tube having a longitudinal axis, said tube comprising a multiplicity of circumferentially oriented fill threads interwoven with a multiplicity of axially oriented, substantially non-elastic warp threads, individual ones of said warp threads defining loops extending radially outwardly from between said fill threads, said loops being set to return to a loop configuration upon release of tension applied axially to said tube, said warp and fill threads together defining an outer, macroscopically smooth, porous surface.

2. The device of claim 1 wherein said threads comprise yarns composed of monofilament fibers.

3. The device of claim 1 wherein said threads comprise a polyethylene terephthalate polymer.

4. The device of claim 1 wherein said threads comprise a non-thrombogenic material.

5. The device of claim 1 wherein surfaces of said threads comprise fluorine.

6. The device of claim 1 having a stretched length between 20% and 70% greater than its unstretched length.

7. The device of claim 1 further comprising a helical winding about said tube.

8. The device of claim 1 having a wall thickness less than about 0.6 mm.

9. The device of claim 2 wherein said fibers are less than about 15 microns in diameter.

10. The device of claim 1 wherein said warp threads comprise a plurality of intertwined yarns.

11. A method of producing a macroscopically smooth elastic tube from a substantially non-elastic microporous woven fabric tube having an inside surface and a longitudinal axis, and comprising circumferentially oriented fill threads interwoven with axially oriented substantially non-elastic warp threads, said method comprising the steps of deforming individual ones of said axially oriented warp threads to define loops extending radially outwardly from between said fill threads, and treating said axially oriented warp threads to set their loop configuration so that said warp threads return to said loop configuration upon release of tension applied axially to said tube.

12. The method of claim 11 wherein said deforming step is conducted by:

placing said tube on a cylindrical mandrel with the inside surface of said tube uniformly in contact therewith; and compacting said tube axially on said mandrel to produce loops in said warp threads extending radially outwardly between said fill threads.

13. The method of claim 11 wherein said treating step is conducted by heating said tube.

14. The method of claim 11 comprising the steps of a. placing said tube on a smooth, cylindrical surface of a mandrel having an outside diameter substantially equal to the inside diameter of said tube to place the inside surface of said tube uniformly in contact with said cylindrical surface;

b. heating said tube on said mandrel;

c. compacting said tube on said mandrel by axially compressing said tube to produce said loops; and d. heating said tube on said mandrel.

15. The method of claim 14 wherein said tube comprises a polyethylene terephthalate polymer.

* * * * *